United States Patent [19]

Crameri et al.

[11] 4,435,585

[45] Mar. 6, 1984

[54] PROCESS FOR THE PREPARATION OF DIHYDROCINNAMALDEHYDE DERIVATIVES

[75] Inventors: Yvo Crameri, Oberwil; Paul A. Ochsner, Geneva; Peter Schudel, Grüt-Wetzikon, all of Switzerland

[73] Assignee: Givaudan Corporation, Clifton, N.J.

[21] Appl. No.: 322,135

[22] Filed: Nov. 17, 1981

[30] Foreign Application Priority Data

Nov. 21, 1980 [CH] Switzerland .................. 8621/80

[51] Int. Cl.$^3$ .................... C07D 317/54; C07C 45/50
[52] U.S. Cl. .................... 549/446; 568/429; 568/592; 568/626; 568/648; 568/442; 568/425; 568/654; 549/445
[58] Field of Search ............... 568/429, 592, 626, 648; 549/446

[56] References Cited

U.S. PATENT DOCUMENTS

| | | | |
|---|---|---|---|
| 2,124,686 | 7/1938 | Carothers et al. | 568/592 |
| 2,189,529 | 2/1940 | Carothers et al. | 568/592 X |
| 2,700,059 | 1/1955 | Hall et al. | 568/592 X |
| 3,965,192 | 6/1976 | Booth | 568/429 |
| 4,107,439 | 8/1978 | Walker et al. | 568/592 |
| 4,113,781 | 9/1978 | Agvila et al. | 568/429 |
| 4,182,730 | 1/1980 | Virgilio et al. | |
| 4,268,688 | 5/1981 | Tinker et al. | 568/429 X |

FOREIGN PATENT DOCUMENTS

| | | |
|---|---|---|
| 8022 | 2/1980 | European Pat. Off. |
| 8459 | 3/1980 | European Pat. Off. |
| 1593663 | 9/1971 | Fed. Rep. of Germany |
| 2235466 | 7/1974 | Fed. Rep. of Germany |
| 2301940 | 8/1974 | Fed. Rep. of Germany |
| 2849742 | 10/1980 | Fed. Rep. of Germany |

OTHER PUBLICATIONS

Sigmund et al., Chemical Abs., vol. 23, (1929), 2416–2417.

Watanabe et al., Bull. Chim. Soc., Japan, 52(9), 2735–2736.

*Primary Examiner*—Bernard Helfin
*Attorney, Agent, or Firm*—Robert F. Tavares

[57] ABSTRACT

There is disclosed a novel process for preparing a number of cinnamaldehyde derivatives. These cinnamaldehyde derivatives can be reduced to dihydrocinnamaldehyde derivatives, a number of which are commercially important in the preparation of fragrances. The invention is also directed to a number of novel intermediates and their preparation.

8 Claims, No Drawings

PROCESS FOR THE PREPARATION OF DIHYDROCINNAMALDEHYDE DERIVATIVES

BACKGROUND OF THE INVENTION

A number of substituted dihydrocinnamaldehydes are known odoriferous substances. W. Berends and L. M. v.d. Linde, Perfumery and Essential Oil Record, 58, 372 (1967). Some of these compounds, particularly p-isopropyl-α-methyldihydrocinnamaldehyde and p-t-butyl-α-methyldihydrocinnamaldehyde, are among the principal aromatic compounds used in the industry.

These compounds are usually made by the multistep process shown below which involves a condensation reaction of an aromatic aldehyde with the α-methylene of an aliphatic aldehyde

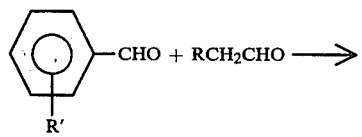

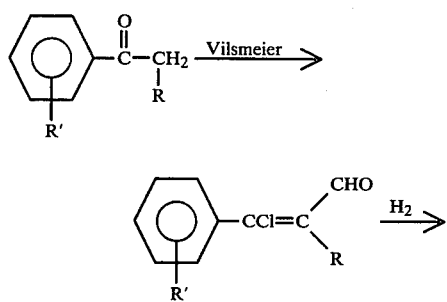

Other methods of synthesis are reviewed in the Berends article above. (R and R' are suitable substituents provided to illustrate the general utility of the prior art processes).

The success of this multistep process necessarily depends on the availability of the appropriate corresponding benzaldehyde and the ability to minimize side reactions such as self condensation of the aliphatic aldehyde and/or the Cannizzaro reaction.

More recently, U.S. Pat. No. 4,182,730 described a method for converting an aryl alkyl ketone to the desired α-alkyldihydrocinnamaldehydes in a process which involves the Vilsmeier reaction as illustrated below.

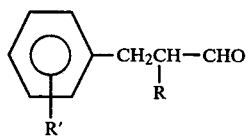

Nothing in the prior art discloses or suggests the novel process and intermediates disclosed herein.

THE INVENTION

This invention is concerned with a novel process for preparing cinnamaldehyde derivatives which can be illustrated as follows:

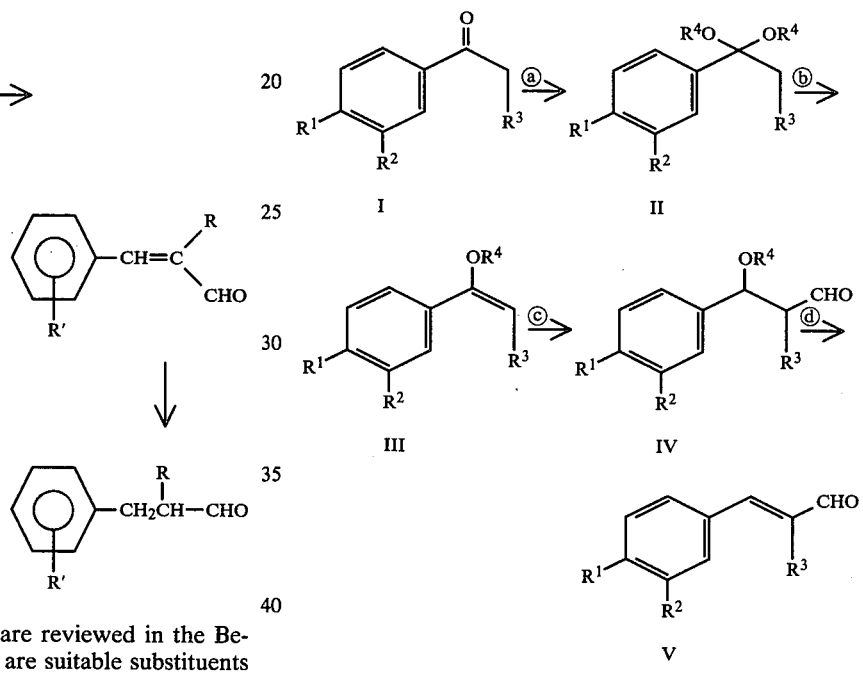

wherein:

$R^1$ represents isopropyl, n-butyl, sec. butyl, isobutyl, tert-butyl, methoxy or, together with $R^2$, represents methylene dioxy;

$R^2$ represents hydrogen, or together with $R^1$, represents methylene dioxy;

$R^3$ represents hydrogen or methyl; and $R^4$ represents methyl or ethyl.

The cinnamaldehyde derivatives can then be hydrogenated by known methods to the corresponding dihydrocinnamaldehydes as illustrated below:

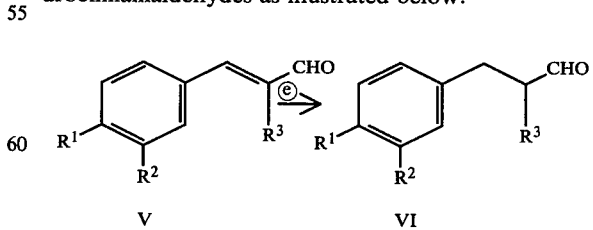

A number of compounds of formula VI are known odorant substances, e.g.

3-(p-isopropylphenyl)-2-methyl-propionaldehyde
3-(p-tert. butylphenyl)-2-methyl-propionaldehyde 3-(3,4-methyleneioxyphenyl)-2-methyl-propionaldehyde
3(p-methoxyphenyl)-2-methyl-propionaldehyde
3-(p-tert.butylphenyl)-propionaldehyde
3-(p-n-butylphenyl)-2-methyl-propionaldehyde,
3-(p-isobutylphenyl)-2-methyl-propionaldehyde and
3-[p-($\alpha$-methylpropyl)-phenyl]-2-methyl-propionaldehyde.

DESCRIPTION OF THE PREFERRED EMBODIMENTS

The first step of the novel sequence (step (a)) involves converting the ketone of formula I to the novel ketal of formula II. The conversion of the ketone to the ketal can be carried out by methods similar to those known in the art, for example, by treating a compound of formula VI with ethanol or methanol and ethyl orthoformate or methyl orthoformate in the presence of catalytic amounts of p-toluene-sulphonic acid. The ketalization is conveniently carried out at room temperature or a slightly higher temperature (e.g. 30°–80° C.).

The novel ketal of formula II can be converted to the enol ether III by an acid-catalyzed elimination of the alcohol $R^4OH$, the alcohol being distilled off as it is formed.

The distillation can be conveniently carried out, e.g. in the case of ethanol, at temperatures of 110° C. to 170° C. with 130° C. to 150° C. being preferred.

When methanol is eliminated, comparable results may be obtained at somewhat lower temperatures.

A key step in the process is step (c) which involves the hydroformylation of the enol ether III to form a novel $\beta$-alkoxy aldehyde of formula IV which can, in turn, be converted to the cinnamaldehyde derivative V by alcohol cleavage, for example acid catalysed alcohol cleavage.

The hydroformylation, in accordance with the invention, can be carried out using carbon monoxide and hydrogen, conveniently in the volume ratio of 1:4 to 4:1 with a volume ratio of 1:3 to 3:1 being preferred. It is advantageous to use this gas mixture in excess based on the starting enol ether of formula III (e.g. up to a 20–100 fold molar amount).

The hydroformylation is preferably carried out at temperatures of 50° to 150° C. Temperatures of 90° to 120° C. have proved to be especially preferred.

The hydroformylation is conveniently carried out under pressures of 150 to 700 atmospheres, with pressures of 250 to 500 atmospheres being preferred.

The hydroformylation is preferably carried out in the presence of rhodium catalysts. Examples of catalysts which are preferred are the pure metal, oxides, salts or complexes, for example
Rh/C (e.g. 5%),
$RhCl_3.H_2O$,
$Rh_2O_3$,
$Rh(PPh_3)_3Cl$,
$RhHCO (PPh_3)_3$,
$RhCO(PPh_3)_2Cl$ and
$Rh_6(CO)_{16}$.

From this compilation, it is evident that the catalysis can be carried out not only in a homogeneous phase but also in a heterogeneous phase. It is preferred to carry out the catalysis in a heterogeneous phase. It is preferred to use 0.01 to 0.5 wt.% rhodium (calculated as the metal) based on the enol ether of formula III with amounts of 0.03 to 0.1 wt.% of rhodium being especially preferred.

The process provided by the invention is carried out, for example, by providing the ether of formula III, optionally together with solvents, introducing the rhodium catalyst in the indicated amounts (e.g. in a pressure autoclave) and, while feeding in the mixture of carbon monoxide and hydrogen in the indicated ratios, carrying out the hydroformylation under the aforementioned temperature and pressure conditions. The hydroformylation can, however, also advantageously be carried out continuously in a suitable apparatus. After cooling, the product is de-pressurized and the excess mixture of carbon monoxide and hydrogen is separated and, if desired, used again, while the liquid product is worked-up according to usual methods (e.g. by distillation), whereby the $\beta$-alkoxy aldehyde of formula IV is obtained as the main product. It is normally not necessary to isolate this product in pure form. For the further processing, it is sufficient merely to separate the catalyst as a sludge in a first distillation and to further process the crude mixture.

The $\beta$-alkoxy-aldehydes of formula IV, which are novel and also form an object of the invention, can be converted by alcohol cleavage (e.g. acid-catalysed alcohol cleavage) into the cinnamic acid derivatives of formula V as shown in step (d).

This alcohol cleavage is conveniently carried out under acid conditions, with mineral acids such as hydrochloric acid or sulfuric acid being especially suitable, and at temperatures between 20° and 100° C., if desired in the presence of an inert solvent (e.g. toluene).

The cinnamaldehyde derivative of formula V may be converted to the dihydrocinnamaldehyde derivatives of formula VI (step (e)) by hydrogenation according to methods known in the art, e.g. using a Pd/C catalyst. See P. Bedoukian, Perfumery & Flavouring Synthetics, Elsevier, Amsterdam, London, New York 1967, 151 or U.S. Pat. No. 2,875,131. The following examples are offered to illustrate the present invention.

EXAMPLE 1

(a) 1.050 liters of 1,2-dichloroethane are placed in a 2½ liter sulphonation flask and thereupon 418 g of aluminium chloride are introduced. The mixture is cooled to 0° C. and, within 1¾ hours, 254 g of propionic acid chloride are added dropwise thereto at 0°–5° C. (ice/acetone cooling). The mixture is left to warm to 18° within 30 minutes and now there are added dropwise thereto 350 g of tert.butylbenzene at 20° within 2 hours. In so doing the mixture is cooled slightly with water. The mixture is stirred for 2 hours and left to stand for 12 hours. Thereafter, the mixture is poured while stirring into a mixture of 1.600 kg of ice, 260 ml of water and 260 ml of concentrated hydrochloric acid, the temperature always being held below 20° C. The aqueous phase is separated and extracted with two 500 ml portions of dichloroethane. The combined organic phases are washed (pH 6) once with 1 liter of water, three times with 400 ml of 2% sodium hydroxide and once with 500 ml of water. The solvent is removed on a rotary evaporator and the residue (505 g) is distilled in vacuo over a 50 cm column.

B.p./0.01 mmHg  −100°—50 g: First runnings.
−102°—425 g: p-Tert.butyl-propiophenone, $n_D^{20}=1.5164$. Residue—20 g.

Boiling point of the pure compound: 92°–94° C./0.04 mmHg
$n_D^{20}$: 1.5184; IR: bands inter alia at 1685 and 1605$^{-1}$ and 800, 950 and 1225 cm$^{-1}$.

(b) 296 g of absolute alcohol and 6.5 g of p-toluenesulphonic acid are placed in a 4½ liter sulphonation flask. 1233 g of p-tert.butyl-propiophenone are added dropwise within 30 minutes. Now, 953 g of triethyl orthoformate are added thereto. The temperature is held at 30° by cooling with water. The mixture is subsequently stirred at 20°-25° for a further 22 hours. The mixture is adjusted to pH 8 with 31 ml of triethylamine and poured while stirring into 300 ml of 5% bicarbonate solution and 500 g of ice. The aqueous phase is extracted once with ether and the organic phase is washed with 5% bicarbonate solution. After adding 1 g of soda, the solution is concentrated on a rotary evaporator. In order to remove the water as completely as possible, 500 ml of methylene chloride are subsequently added and the mixture is evaporated once more. The residue is distilled in vacuo over a 15 cm Vigreux column with the addition of 1 g of soda.

B.p. 0.05 mm −92°—27 g: First runnings. ∼92°—1600 g: p-Tert.butyl-propiophenone diethyl ketal; $n_D^{20}=1.4821$ (94.1%). Residue—15 g.

Boiling point of the pure compound: 102°/0.2 mmHg; $n_D^{20}=1.4830$; IR: bands inter alia at 835, 975, 1050, 1090, 1120 and 1170 cm$^{-1}$.

In the distillation some enol ether is already obtained from the ethyl ketal.

(c) 500 g of p-tert.butyl-propiophenone diethyl ketal and 6 g of p-toluenesulphonic acid are heated (oil bath, 140°) in a distillation apparatus fitted with a 15 cm Vigreux column. The alcohol formed is distilled off continuously. 100 ml of alcohol can be distilled off within 3 hours. The mixture is now evaporated under a water-jet vacuum and the residue is subsequently distilled in a high vacuum.

B.p. 0.05 mmHg −90°—10 g: First runnings. 91°—352 g: p-Tert.butyl-propiophenone enol ethyl ether, $n_D^{20}=1.5160$ (85.2%). Residue 55 g (polymerised).

Boiling point of pure compound: 93°/0.01 mmHg; $n_D^{20}=1.5153$; IR: bands inter alia at 850 and 1070 cm$^{-1}$.

(d) A solution of 0.135 g (0.127 mmol) of Rh$_6$(CO)$_{16}$ and 109 g (416 mmol) of 83.3% of the above enol ether in 100 ml of benzene is charged under argon into a 500 ml Uhde stirring autoclave evacuated four times to 1 mbar and in each case gasified with argon. The autoclave is pressurized to 240 bar with carbon monoxide and hydrogen in the ratio of 3:1. The mixture is heated to 90° C. while stirring. The pressure increases to 290 bar upon heating.

The course of the hydroformylation is followed by gas chromatography. After completion of the hydroformylation the mixture is cooled to room temperature. The mixture is rinsed from the autoclave and evaporated in a rotary evaporator at 60° C. and under a water-jet vacuum. The brown oily product (119.7 g) is gently distilled (1 mbar, 125° C. bath temperature) in order to separate the catalyst and gives 100.2 g of hydroformylation product as a yellow oil which, in accordance with analysis by gas chromatography, consists of 62.1% of the 2-formyl compound, namely 1-(p-tert.butylphenyl)-1-ethoxy-2-formyl-propane. In addition, a small amount of the corresponding 1-formyl compound, namely 1-(p-tert.butylphenyl)-1-ethoxy-1-formyl-propane, is obtained. This fact can be proved by the IR-spectrum and NMR-spectrum.

(e) 100.2 g of distilled hydroformylation mixture are stirred with 2 ml (15.4 mmol) of concentrated hydrochloric acid for 6 hours at 50° C. As soon as the entire 2-formyl compound of formula I has reacted (as shown by the analysis of a sample by gas chromatography), the resulting ethyl alcohol is removed by evaporation in a rotary evaporator at 60° C. and under a water-jet vacuum and the mixture (91.4 g) is neutralized with the addition of 1.5 g (90 mmol) of pyridine and distilled over a 25 cm Vigreux column with a vacuum mantle in a high vacuum (0.07 mbar). At a boiling range of 75°-80° there are obtained 41.7 g of 1-(p-tert.butylphenyl)-2-formyl-1-propene. M.p. (from hexane) 68°-70° C.

(f) 1420 g of 1-(p-tert.butylphenyl)-2-formyl-1-propene, prepared as described in paragraph (e), are mixed together with 6 g of 5% palladium/carbon and 6.8 g of soda in 20 ml of water at 70°-75° C. in a stirring autoclave. The autoclave is charged with hydrogen (8 atmospheres) and heated to 110° C. About 230 liters of hydrogen are absorbed after 12 hours. The crude 3-(p-tert.butyl-phenyl)-2-methyl-propionaldehyde is treated with ether, washed neutral with water and dried over sodium sulphate. After removing the ether, the product is fractionally distilled in vacuo. After separating a first running and a last running, there are obtained 1275 g of 3-(p-tert.butylphenyl)-2-methyl-propionaldehyde in 95% purity (about 88% of theory). Boiling point: 150°-152° C./15 mmHg; $n_D^{20}=1.5050$.

EXAMPLE 2

(a) p-Isopropyl-propiophenone 525 ml of 1,2-dichloroethane and 209 g of aluminium chloride are added to a round flask, which is fitted with a stirrer, thermometer, condenser and dropping funnel. The mixture is cooled to 0° C. and 127 g of propionic acid chloride are allowed to drop in at 0°-5° C. within ¾ hour. After the addition, the temperature is allowed to rise to +18° C. and then 157 g of cumene are added within 2 hours at 30° C. The mixture is left to stand for 12 hours and the product is then poured into a mixture of 800 g of ice, 130 ml of water and 130 ml of concentrated hydrochloric acid. The aqueous phase is separated and extracted with two 250 ml portions of dichloroethane. The combined organic phases are washed with three 200 ml portions of 2% sodium hydroxide and with 250 ml of water. The solvent is removed by evaporation under a vacuum and the residue (244 g) is distilled over a 10 cm column. There are obtained 192.1 g of p-isopropyl-propiophenone (yield: 83.2% of theory). B.p.=76°-77° C./0.15 mmHg; $n_D^{20}=1.5150$; $d_4^{20}=0.9645$.

(b) p-Isopropyl-propiophenone diethyl ketal 48 ml of absolute ethanol and 1 g of p-toluenesulphonic acid are placed in a round flask which is fitted with a stirrer, thermometer, condenser and dropping funnel. Now, there are added dropwise within 30 minutes while stirring 181.5 g of p-isopropyl-propiophenone and subsequently within 1 hour 152.5 g of triethyl orthoformate. The temperature is held at 30° C. by external cooling. The mixture is subsequently stirred for a further 22 hours at 20°-25° C. The mixture is then adjusted to pH 8 with 5 g of triethylamine and thereupon poured into 50 ml of 5% bicarbonate solution and 80 g of ice. The aqueous phase is separated and extracted with ether. The combined organic phases are washed with 5% bicarbonate solution and, after the addition of 0.3 g of sodium carbonate, the solvent is removed by evaporation under a vacuum and the residue is distilled over a 15 cm column. There are obtained 193.6 g of p-isopropyl-propiophenone diethyl ketal (yield: 75.1% of theory). B.p.=66° C./0.05 mmHg; $n_D^{20}=1,4778$; $d_4^{20}=0,9305$.

(c) 1-p-Isopropylphenyl-1-ethoxy-1-propene 150 g of p-isopropyl-propiophenone diethyl ketal are treated with 1.5 g of p-toluenesulphonic acid and heated in a distillation apparatus to 140° C. (oil bath temperature). The alcohol formed is distilled off continuously at atmospheric pressure. 20 g of ethanol are distilled off within 3 hours. Now, the mixture is evaporated further under a water-jet vacuum and subsequently distilled in a high vacuum over a 30 cm column. There are obtained 50.6 g of 1-(p-isopropylphenyl)-1-ethoxy-1-propene (yield: 41.4%). B.p.=71°-72° C./0.1 mmHg; $n_D^{20}=1.5093$; $d_4^{20}=0.9324$.

The hydroformylation of the enol ether is carried out at 100° C., but otherwise in the same manner as described in Example 1. The same is also true for the subsequent steps in which the conditions described in Example 1 can likewise be used. The yields are analogous to those of Example 1.

EXAMPLE 3

(a) p-Methoxy-propiophenone 525 ml of 1,2-dichloroethane and 209 g of aluminium chloride are added to a round flask which is fitted with a stirrer, thermometer, condenser and dropping funnel. The mixture is cooled to 0° C. and 127 g of propionic acid chloride are allowed to drop in at 0°-5° C. within 75 minutes. After the addition, the temperature is allowed to rise to 18° C. and then 141.6 g of anisole are added within 2 hours and at 20° C. The mixture is left to stand for 12 hours and then the product is poured into a mixture of 800 g of ice, 130 ml of water and 130 ml of concentrated hydrochloric acid. The aqueous phase is separated and extracted with two 250 ml portions of 1,2-dichloroethane. The combined organic phases are washed with three 200 ml portions of 2% sodium hydroxide and with 250 ml of water. The solvent is removed by evaporation under a vacuum and the residue (198 g) is distilled over a 25 cm column. There are obtained 143 g of p-methoxy-propiophenone (yield: 66.4% of theory). B.p.=90° C./0.4 mmHg; melting point 26° C.; $n_D^{20}=1.5451$; $d_4^{20}=0.9645$.

(b) p-Methoxy-propiophenone diethyl ketal 40 ml of absolute ethanol and 0.75 g of p-toluenesulphonic acid are placed in a round flask which is fitted with a stirrer, thermometer, condenser and dropping funnel. Now, there are added dropwise within 15 minutes while stirring 120 g of p-methoxy-propiophenone and subsequently within 1 hour 108 g of triethyl orthoformate. The temperature is held below 3° C. The mixture is subsequently stirred for a further 22 hours at room temperature. The mixture is adjusted to pH 8 with 3.6 g of triethylamine and then poured into 40 ml of 5% bicarbonate solution and 60 g of ice. The aqueous phase is separated and extracted with ether. The combined organic phases are washed with 5% bicarbonate solution and, after the addition of 0.2 g of sodium carbonate, the solvent is removed by evaporation under a vacuum and the residue is distilled over a 15 cm column. There are obtained 36.7 g of p-methoxy-propiophenone diethyl ketal (yield: 21% of theory). B.p.=83°-84° C./0.4 mmHg; $n_D^{20}=1.4858$; $d_4^{20}=0.9988$.

(c) 1-(p-Methoxyphenyl)-1-ethoxy-1-propene 103.3 g of p-methoxy-propiophenone diethyl ketal are treated with 1.1 g of p-toluenesulphonic acid and heated in a distillation apparatus to 140° C. (oil bath temperature). In so doing, the ethanol formed is distilled off continuously at atmospheric pressure. 20 g of ethanol are distilled off within 3½ hours. Subsequently, the mixture remaining is distilled in a high vacuum over a 15 cm column. There are obtained 62.2 g of 1-(p-methoxyphenyl)-1-ethoxy-1-propene (yield: 74.8% of theory). B.p.=78°-79° C. 0.3 mmHg; $n_D^{20}=1.5315$; $d_4^{20}=1.0175$.

The hydroformylation is carried out at 130° C., but otherwise in the same manner as described in Example 1. The same is true for the subsequent steps. The yields are analogous.

We claim:

1. A process for the manufacture of a compound of the formula

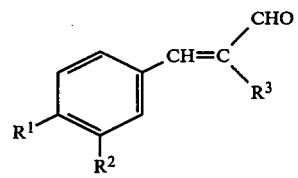

wherein:

$R^1$ represents isopropyl, n-butyl, sec. butyl, isobutyl, tert. butyl, methoxy or, together with $R^2$, represents methylene dioxy;

$R^2$ represents hydrogen or, together with $R^1$, represents methylenedioxy; and $R^3$ represents hydrogen or methyl which comprises:

(a) converting a ketone of the formula

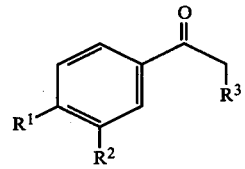

to the corresponding ketal

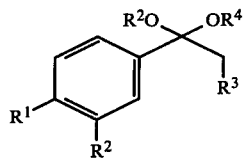

wherein $R^4$ is methyl or ethyl;

(b) converting said ketal by means of an alcohol cleavage, to the corresponding enol ether

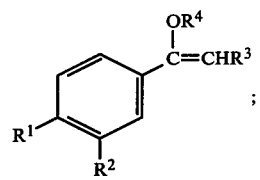

;

(c) converting said enol ethers to the corresponding β-alkoxy aldehyde

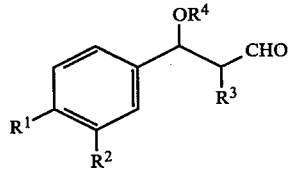

by means of a hydroformylation reaction, and (d) subjecting said β-alkoxy aldehyde to an alcohol cleavage, wherein the hydroformylation is carried out by reacting said enol ether with carbon monoxide and hydrogen in the presence of a rhodium catalyst wherein:

(a) the ratio of carbon monoxide to hydrogen is between 1 to 4 and 4 to 1;

(b) the temperature is between 50° C. and 150° C; and (c) the pressure is between 150 and 700 atmospheres.

2. A process according to claim 1 wherein the rhodium catalyst is selected from the group consisting of Rh/C, $RhCl_3 \cdot H_2O$, $Rh_2O_3$, $Rh(PPh_3)_3Cl$, $RhHCO(PPh_3)_3$, $RhCO(PPh_3)_2Cl$ and $Rh_6(CO)_{16}$.

3. A process according to claim 2 wherein the catalyst is used at a level of 0.01 to 0.5 weight percent of the enol to be hydroformylated.

4. A process according to claims 1, 2 or 3 wherein the catalyst used is $Rh_6(CO)_{16}$ or Rh/C.

5. A process for preparation of β-alkoxy dihydrocinnamaldehyde of the formula

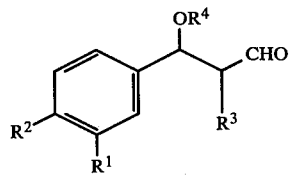

wherein:

$R^1$ represents isopropyl, n-butyl, sec. butyl, isobutyl, tert. butyl, methoxy or, together with $R^2$, represents methylene dioxy;

$R^2$ represents hydrogen or, together with $R^1$, represents methylene dioxy;

$R^3$ represents hydrogen or methyl; and $R^4$ represents methyl or ethyl which comprises reacting a compound of the formula

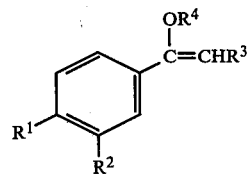

with carbon monoxide and hydrogen in the presence of a rhodium catalyst wherein (a) the ratio of carbon monoxide to hydrogen is between 1 to 4 and 4 to 1, (b) the temperature is between 50° C. and 150° C., and (c) the pressure is between 150 and 700 atmosphere.

6. A process according to claim 5 wherein the rhodium catalyst is selected from the group consisting of Rh/C, $RhCl_3 \cdot H_2O$, $Rh_2O_3$, $Rh(PPh_3)_3Cl$, $RhHCO(PPh_3)_3$, $RhCO(PPh_3)_2Cl$ and $Rh_6(CO)_{16}$.

7. A process according to claim 6 wherein the catalyst is used at a level of 0.01 to 0.5 weight percent of the enol ether to be hydroformylated.

8. A process according to claims 5, 6 or 7 wherein the catalyst used is $Rh_6(CO)_{16}$ or Rh/C.

* * * * *